(12) United States Patent
Kalpin et al.

(10) Patent No.: US 8,568,389 B2
(45) Date of Patent: *Oct. 29, 2013

(54) ESTIMATING THE VOLUME OF FLUID IN THERAPEUTIC FLUID DELIVERY DEVICE RESERVOIR

(75) Inventors: Scott L. Kalpin, Harris, MN (US); Michael D. Baudino, Coon Rapids, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/438,112

(22) Filed: Apr. 3, 2012

(65) Prior Publication Data

US 2012/0265144 A1 Oct. 18, 2012

Related U.S. Application Data

(63) Continuation of application No. 13/085,573, filed on Apr. 13, 2011, now Pat. No. 8,206,378.

(51) Int. Cl.
*A61K 9/22* (2006.01)
*A61M 37/00* (2006.01)

(52) U.S. Cl.
USPC .............. 604/891.1; 604/288.01; 604/288.02; 604/288.04; 73/149

(58) Field of Classification Search
USPC ................ 604/890.1, 891.1, 288.01–288.04; 417/472; 73/157, 149
See application file for complete search history.

(56) References Cited

U.S. PATENT DOCUMENTS

| | | | |
|---|---|---|---|
| 4,373,527 A | 2/1983 | Fischell | |
| 4,395,259 A | 7/1983 | Prestele et al. | |
| 4,443,218 A | 4/1984 | DeCant, Jr. et al. | |
| 4,486,190 A | 12/1984 | Reinicke | |
| 4,561,298 A | 12/1985 | Pond | |
| 4,581,018 A | 4/1986 | Jassawalla et al. | |
| 4,718,430 A | 1/1988 | Holzer | |
| 4,784,645 A | 11/1988 | Fischell | |
| 4,840,064 A | 6/1989 | Fudim | |
| 5,006,997 A | 4/1991 | Reich | |
| 5,088,983 A | 2/1992 | Burke | |

(Continued)

FOREIGN PATENT DOCUMENTS

EP 0622615 A1 11/1994
EP 1649884 A1 4/2006

(Continued)

OTHER PUBLICATIONS

PCT/US2012/023213: International Search Report and Written Opinion dated Jul. 17, 2012.

(Continued)

*Primary Examiner* — Nicholas Lucchesi
*Assistant Examiner* — Leah Stohr
(74) *Attorney, Agent, or Firm* — Shumaker & Sieffert, P.A.

(57) ABSTRACT

A number of parameters related to the operation of a fluid delivery device are determined based on pressures within the device sensed using multiple pressure sensors. In one example, the volume of therapeutic fluid within a reservoir of a fluid delivery device is estimated based on a measured pressure differential. In another example, the rate at which a therapeutic fluid is added to or removed from the reservoir is estimated based on the measured pressure differential.

26 Claims, 5 Drawing Sheets

(56) References Cited

U.S. PATENT DOCUMENTS

| | | | |
|---|---|---|---|
| 5,132,923 A | 7/1992 | Crawford et al. | |
| 5,319,964 A | 6/1994 | Stephenson et al. | |
| 5,507,737 A | 4/1996 | Palmskog | |
| 5,904,666 A | 5/1999 | DeDecker et al. | |
| 5,974,873 A | 11/1999 | Nelson | |
| 6,152,898 A | 11/2000 | Olsen | |
| 6,302,864 B1 | 10/2001 | Nowosielski | |
| 6,315,769 B1 | 11/2001 | Peer et al. | |
| 6,321,597 B1 | 11/2001 | Demers et al. | |
| 6,482,177 B1 | 11/2002 | Leinders | |
| 6,542,350 B1 | 4/2003 | Rogers | |
| 6,542,848 B1 | 4/2003 | Neeser et al. | |
| 6,562,001 B2 | 5/2003 | Lebel et al. | |
| 6,740,059 B2 | 5/2004 | Flaherty | |
| 6,810,308 B2 | 10/2004 | Shajii et al. | |
| 6,939,111 B2 | 9/2005 | Huitt et al. | |
| 7,054,782 B2 | 5/2006 | Hartlaub | |
| 7,137,964 B2 | 11/2006 | Flaherty | |
| 7,206,715 B2 | 4/2007 | Vanderveen et al. | |
| 7,481,763 B2 | 1/2009 | Hassler, Jr. et al. | |
| 7,505,869 B2 | 3/2009 | Hartlaub | |
| 8,313,308 B2 | 11/2012 | Lawless et al. | |
| 2002/0087116 A1 | 7/2002 | Hartlaub | |
| 2002/0161328 A1 | 10/2002 | Rogers | |
| 2003/0084589 A1 | 5/2003 | Chowdhury et al. | |
| 2004/0249336 A1 | 12/2004 | Faries et al. | |
| 2004/0260233 A1 | 12/2004 | Garibotto et al. | |
| 2005/0075624 A1 | 4/2005 | Miesel | |
| 2005/0187515 A1 | 8/2005 | Varrichio et al. | |
| 2006/0089619 A1 | 4/2006 | Ginggen | |
| 2006/0149220 A1 | 7/2006 | Ullestad et al. | |
| 2006/0276744 A1 | 12/2006 | Falk | |
| 2007/0068528 A1 | 3/2007 | Bohm et al. | |
| 2007/0106280 A1 | 5/2007 | Utard et al. | |
| 2007/0239381 A1 | 10/2007 | Ginggen et al. | |
| 2007/0250045 A1 | 10/2007 | Trieu | |
| 2007/0255259 A1 | 11/2007 | Miesel | |
| 2008/0125702 A1 | 5/2008 | Blischak et al. | |
| 2008/0243093 A1 | 10/2008 | Kalpin et al. | |
| 2009/0082757 A1 | 3/2009 | Rogers et al. | |
| 2009/0270844 A1 | 10/2009 | Seeley et al. | |
| 2010/0125246 A1 | 5/2010 | Kalpin | |
| 2010/0137842 A1* | 6/2010 | Gibson | 604/890.1 |
| 2010/0288788 A1 | 11/2010 | Ophardt | |
| 2011/0257591 A1 | 10/2011 | Nelson Konen et al. | |
| 2011/0257907 A1 | 10/2011 | Kalpin | |

FOREIGN PATENT DOCUMENTS

| | | | |
|---|---|---|---|
| EP | 1839635 A1 | 10/2007 | |
| WO | WO00/072900 | 12/2000 | |
| WO | WO 02/28454 A2 | 4/2002 | |
| WO | WO03/068049 | 8/2003 | |
| WO | WO 2007/041471 A2 | 4/2007 | |
| WO | WO 2008/121421 A1 | 10/2008 | |
| WO | WO 2009/137780 A2 | 11/2009 | |
| WO | WO 2010/059588 A1 | 5/2010 | |

OTHER PUBLICATIONS

Office action for U.S. Appl. No. 12/762,108, mailed Jan. 7, 2013, 27 pages.
Response to office action for U.S. Appl. No. 12/762,108, filed Apr. 8, 2013, 18 pages.
International Search Report and the Written Opinion of international patent application No. PCT/US2011/023086, mailed Oct. 12, 2011, 16 pp.
Notice of Allowance from U.S. Appl. No. 13/085,573, dated Jan. 23, 2012, 12 pp.
Post-Allowance Communication for U.S. Appl. No. 13/085,573, filed Apr. 23, 2012, 2 pp.
Notice of Allowance from U.S. Appl. No. 13/085,573, dated May 25, 2012, 2 pp.
Restriction Requirement from U.S. Appl. No. 12/762,064, dated Apr. 4, 2011, 6 pp.
Response to Restriction Requirement dated Apr. 4, 2011, from U.S. Appl. No. 12/762,064, filed May 3, 2011, 3 pp.
Office Action from U.S. Appl. No. 12/762,064, dated Aug. 12, 2011, 27 pp.
Response to Office Action dated Aug. 12, 2011, from U.S. Appl. No. 12/762,064, filed Nov. 11, 2011, 26 pp.
Final Office Action from U.S. Appl. No. 12/762,064, dated Mar. 5, 2012, 27 pp.
Response to Final Office Action dated Mar. 5, 2012, from U.S. Appl. No. 12/762,064, filed May 4, 2012 (with RCE), 26 pp.
Office Action from U.S. Appl. No. 12/619,145, dated Jun. 11, 2010, 11 pp.
Response to Office Action dated Jun. 11, 2010, from U.S. Appl. No. 12/619,145, filed Oct. 8, 2010, 9 pp.
Office Action from U.S. Appl. No. 12/619,145, dated Dec. 28, 2010, 12 pp.
Response to Office Action dated Dec. 28, 2010, from U.S. Appl. No. 12/619,145, filed Mar. 28, 2011, 7 pp.
Final Office Action from U.S. Appl. No. 12/619,145, dated Jun. 24, 2011, 11 pp.
Response to Final Office Action dated Jun. 24, 2011, from U.S. Appl. No. 12/619,145, filed Sep. 7, 2011 (with RCE), 7 pp.
U.S. Appl. No. 13/087,755, by John M. Gray, filed Apr. 15, 2011.
Office action from U.S. Appl. No. 12/762,108, dated Aug. 6, 2013, 30 pp.
Office action from U.S. Appl. No. 12/762,121, dated Aug. 6, 2013, 21 pp.

\* cited by examiner

ESTIMATING THE VOLUME OF FLUID IN THERAPEUTIC FLUID DELIVERY DEVICE RESERVOIR

This application is a continuation of U.S. application Ser. No. 13/085,573, filed Apr. 13, 2011, the entire content of which is incorporated herein by reference.

BACKGROUND

A variety of medical devices are used for chronic, i.e., long-term, delivery of fluid therapy to patients suffering from a variety of conditions, such as chronic pain, tremor, Parkinson's disease, epilepsy, urinary or fecal incontinence, sexual dysfunction, obesity, spasticity, or gastroparesis. For example, pumps or other fluid delivery devices can be used for chronic delivery of therapeutic fluids, such as drugs to patients. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device that can deliver a drug or other therapeutic fluid to a patient at a selected site. A drug infusion device may be partially or completely implanted at a location in the body of a patient and deliver a fluid medication through a catheter to a selected delivery site in the body. Drug infusion devices, such as implantable drug pumps, commonly include a reservoir for holding a supply of the therapeutic fluid, such as a drug, for delivery to a site in the patient. The fluid reservoir can be self-sealing and accessible through one or more ports. A pump is fluidly coupled to the reservoir for delivering the therapeutic fluid to the patient. A catheter provides a pathway for delivering the therapeutic fluid from the pump to the delivery site in the patient.

SUMMARY

In general, this disclosure describes techniques for estimating the volume of a therapeutic fluid in the reservoir of an implantable fluid delivery device using a pressure differential between multiple measured pressures.

In one example, a method includes measuring a pressure within a therapeutic fluid reservoir of an implantable fluid delivery device, measuring a pressure within a chamber of the fluid delivery device at least partially surrounding the reservoir, and estimating a volume of a therapeutic fluid within the reservoir based on a pressure differential between the measured pressure within the reservoir and the measured pressure within the propellant gas chamber.

In another example, a fluid delivery system includes an implantable fluid delivery device, a reservoir, a chamber, a first pressure sensor, a second pressure sensor, and a processor. The reservoir is configured to store a therapeutic fluid. The chamber at least partially surrounds the reservoir. The first pressure sensor is configured to sense a pressure within the reservoir. The second pressure sensor is configured to sense a pressure within the chamber. The processor is configured to measure the pressure within the reservoir with the first pressure sensor, measure the pressure within the chamber with the second pressure sensor, and estimate a volume of a therapeutic fluid within the reservoir based on a pressure differential between the measured pressure within the reservoir and the measured pressure within the chamber.

In another example, a computer-readable storage medium includes instructions for causing a programmable processor to measure a pressure within a therapeutic fluid reservoir of an implantable fluid delivery device, measure a pressure within a chamber of the fluid delivery device at least partially surrounding the reservoir, and estimate a volume of a therapeutic fluid within the reservoir based on a pressure differential between the measured pressure within the reservoir and the measured pressure within the chamber.

In another example, a system includes means for measuring a pressure within a therapeutic fluid reservoir of an implantable fluid delivery device, means for measuring a pressure within a chamber of the fluid delivery device at least partially surrounding the reservoir, and means for estimating a volume of a therapeutic fluid within the reservoir based on a pressure differential between the measured pressure within the reservoir and the measured pressure within the chamber.

The details of one or more examples disclosed herein are set forth in the accompanying drawings and the description below. Other features, objects, and advantages will be apparent from the description and drawings, and from the claims.

DETAILED DESCRIPTION

This application is related to U.S. patent application Ser. No. 12/619,145, filed Nov. 16, 2009, which claims the benefit of U.S. Provisional Application Ser. No. 61/116,309, filed Nov. 20, 2008, both of which applications are incorporated herein by this reference. This application is also related to U.S. patent application Ser. No. 12/199,536, filed Aug. 27, 2008, which claims the benefit of U.S. Provisional Application Ser. No. 60/975,286, filed Sep. 26, 2007, both of which applications are incorporated herein by this reference. This application is also related to U.S. patent application Ser. No. 12/762,108, U.S. patent application Ser. No. 12/762,121, and U.S. application Ser. No. 12/762,064, all of which were filed on Apr. 16, 2010 and are incorporated herein by this reference.

It is generally useful for the safe and intended operation of implantable fluid delivery devices (hereinafter IMD or device) to monitor the volume of therapeutic fluid in the reservoir of the device as the fluid is being delivered to a patient. For example, it is useful to have an actual measurement or an estimate derived from measured values of the volume of therapeutic fluid in the reservoir of an IMD. Fluid volume has been determined in the past by calculating the volume based on an initial fill volume in the reservoir minus the amount of fluid dispensed to the patient over time. However, neither the fill volume nor the amount of fluid dispensed over time in such examples is measured. Instead, the fill volume is commonly specified by a user, e.g. entered via an external programmer, and thus is subject to human error.

Additionally, the amount of fluid dispensed over time is a theoretical calculation based on an expected dispense rate or volume programmed into the device, which assumes perfectly consistent operation of the IMD over time, e.g. assumes that the device dispenses fluid at the same rate at all times.

It may also be useful to verify that a clinician has correctly accessed a refill port of an IMD and is actually filling the reservoir with therapeutic fluid to prevent an unintended injection of the fluid into a tissue pocket within a patient. Additionally, it may be useful to monitor the fill status of the reservoir of such devices to detect unexpected changes in the amount of fluid in the device. An unexpected change in fluid volume may occur when a patient or another person, outside of a clinical environment, attempts to access the refill port of the reservoir to remove therapeutic fluid from the device. Another cause of unexpected changes in fluid volume in the reservoir may be valve leakage or pump stroke volume variation. Unexpected changes in reservoir volume may affect the operation of the device by causing underdosing or overdosing of the patient with the therapeutic fluid delivered by the IMD. Underdosing of a patient may be of particular interest in cases where rapidly reducing the amount of therapeutic fluid delivered by the device to the patient may cause withdrawal symptoms. Device awareness of reservoir fill status is important for these and other reasons related to the proper operation of IMDs and the efficacious delivery of therapy to patients by such devices.

Although different mechanisms are capable of determining the volume of therapeutic fluid in the reservoir of an IMD, one convenient and economical method is to employ a pressure sensor that monitors pressure within the device over time. Generally speaking, the volume of the reservoir of an IMD may be extrapolated from a sensed pressure. However, the relationship between sensed pressure and reservoir fluid volume varies with temperature, which may not be constant. For example, in the event the temperature of a therapeutic fluid added to the reservoir of an IMD is not the same as the reservoir temperature, fluid volume will depend both on pressure changes and temperature changes. Therefore, it also may be necessary, in temperature-dependent applications, to determine one or more temperatures related to filling the reservoir of an IMD with a therapeutic fluid. In particular, it may be necessary for the proper monitoring of reservoir volume to determine the temperature of the reservoir of the IMD, which may, in some examples, be equated to the temperature of the gas propellant used to pressurize the reservoir of the device and the temperature of therapeutic fluid added to the reservoir.

One challenge with extrapolating reservoir volume from pressure in temperature-dependent applications is that the temperatures of the reservoir of the IMD and the therapeutic fluid are unknown. Both temperatures may be measured by employing additional sensors, such as temperature sensors to directly measure temperature. However, incorporation of additional sensors may add cost and complexity to the IMD. Measuring temperatures directly may also complicate the process of refilling an IMD with therapeutic fluid, because, e.g., a user, such as a clinician may be required to measure and then enter the fluid temperature into a programmer to be transmitted to the IMD. Finally, even direct temperature measurement may involve analytical complications, as thermodynamic effects on temperature and pressure changes in the IMD must be accounted for with respect to the measurements taken by some temperature sensors employed to measure the temperature of the reservoir and/or the fluid.

Examples according to this disclosure, instead of accounting for temperature effects in volume estimations based on pressure measurements, employ techniques that substantially remove the temperature effects from the volume estimation. Removing the temperature effects from volume estimations may function to remove costs and complexities of analytically and/or instrumentally accounting for changes of the temperature of the reservoir of an IMD. The manner by which temperature effects are removed in the following examples is by estimating the volume of a therapeutic fluid in the reservoir of an IMD using a pressure differential based on multiple pressure measurements. Each of the pressures measured are affected equally by temperature effects, but only one is affected by fluid volume changes. As such, the differential of the two measured pressures cancels the temperature effects, while retaining the volume effects. Thus, the differential pressure measurement is proportional to the volume of fluid in the reservoir of the device and this estimation of volume is substantially unaffected by temperature changes.

Figure 1:
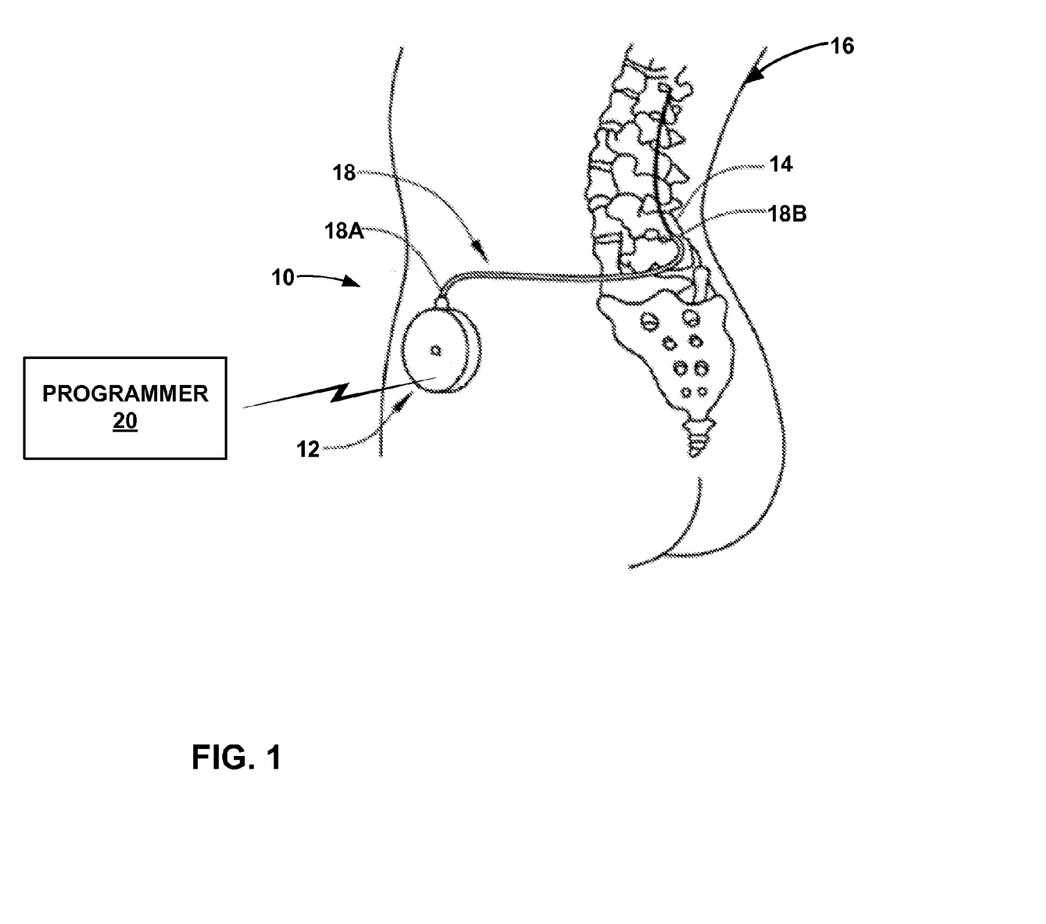
FIG. 1 is a conceptual diagram illustrating an example of a fluid delivery system including an implantable fluid delivery device configured to deliver a therapeutic fluid to a patient via a catheter.

FIG. 1 is a conceptual diagram illustrating an example of a therapy system 10, which includes implantable medical device (IMD) 12, catheter 18, and external programmer 20. IMD 12 is connected to catheter 18 to deliver at least one therapeutic fluid, e.g. a pharmaceutical agent, pain relieving agent, anti-inflammatory agent, gene therapy agent, or the like, to a target site within patient 16. IMD 12 includes an outer housing that, in some examples, is constructed of a biocompatible material that resists corrosion and degradation from bodily fluids including, e.g., titanium or biologically inert polymers. IMD 12 may be implanted within a subcutaneous pocket relatively close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic fluid. In still other examples, IMD 12 may be external to patient 16 with a percutaneous catheter connected between IMD 12 and the target delivery site within patient 16.

IMD 12 delivers a therapeutic fluid from a reservoir (not shown) to patient 16 through catheter 18 from proximal end 18A coupled to IMD 12 to distal end 18B located proximate to the target site. Example therapeutic fluids that may be delivered by IMD 12 include, e.g., insulin, morphine, hydromorphone, bupivacaine, clonidine, other analgesics, baclofen and other muscle relaxers and antispastic agents, genetic agents, antibiotics, nutritional fluids, hormones or hormonal drugs, gene therapy drugs, anticoagulants, cardiovascular medications or chemotherapeutics.

Catheter 18 can comprise a unitary catheter or a plurality of catheter segments connected together to form an overall catheter length. External programmer 20 is configured to wirelessly communicate with IMD 12 as needed, such as to provide or retrieve therapy information or control aspects of therapy delivery (e.g., modify the therapy parameters such as rate or timing of delivery, turn IMD 12 on or off, and so forth) from IMD 12 to patient 16.

Catheter 18 may be coupled to IMD 12 either directly or with the aid of a catheter extension (not shown in FIG. 1). In the example shown in FIG. 1, catheter 18 traverses from the implant site of IMD 12 to one or more targets proximate to spinal cord 14. Catheter 18 is positioned such that one or more fluid delivery outlets (not shown in FIG. 1) of catheter 18 are proximate to the targets within patient 16. In the example of FIG. 1, IMD 12 delivers a therapeutic fluid through catheter 18 to targets proximate to spinal cord 14.

IMD 12 can be configured for intrathecal drug delivery into the intrathecal space, as well as epidural delivery into the epidural space, both of which surround spinal cord 14. In some examples, multiple catheters may be coupled to IMD 12 to target the same or different nerve or other tissue sites within patient 16, or catheter 18 may include multiple lumens to deliver multiple therapeutic fluids to the patient. Therefore, although the target site shown in FIG. 1 is proximate to spinal cord 14 of patient 16, other applications of therapy system 10 include alternative target delivery sites in addition to or in lieu of the spinal cord of the patient.

Programmer 20 is an external computing device that is configured to communicate with IMD 12 by wireless telemetry. For example, programmer 20 may be a clinician programmer that the clinician uses to communicate with IMD 12 and program therapy delivered by the IMD. Alternatively, programmer 20 may be a patient programmer that allows patient 16 to view and modify therapy parameters associated with therapy programs. The clinician programmer may include additional or alternative programming features than the patient programmer. For example, more complex or sensitive tasks may only be allowed by the clinician programmer to prevent patient 16 from making undesired or unsafe changes to the operation of IMD 12. Programmer 20 may be a handheld or other dedicated computing device, or a larger workstation or a separate application within another multi-function device.

In examples according to this disclosure, IMD 12, alone or in cooperation with programmer 20 or another device communicatively connected to IMD 12, is configured to measure a pressure within a reservoir of the IMD, measure a pressure within a chamber housing propellant gas employed to equalize pressure in the reservoir, and estimate a volume of a therapeutic fluid within the reservoir based on a pressure differential between the pressure within the reservoir and the pressure within the propellant gas chamber. In one example, IMD 12 may include a reservoir configured to store a therapeutic fluid and a chamber at least partially surrounding the reservoir and configured to be filled with a propellant gas that modulates the pressure within the reservoir. In one example, the propellant gas is employed to maintain a substantially constant pressure within the reservoir in order to deliver the therapeutic fluid to patient 16 consistently and accurately over time. IMD 12 may also include a first pressure sensor configured to sense a pressure within the reservoir and a second pressure sensor configured to sense a pressure within the propellant gas chamber. In one example, a processor of IMD 12 may be configured to measure the pressure within the reservoir with the first pressure sensor, measure the pressure within the chamber with the second pressure sensor, and estimate a volume of a therapeutic fluid within the reservoir based on the pressure differential between the pressure within the reservoir and the pressure within the chamber.

IMD 12 may also control a fluid volume gauge to indicate the estimated volume of therapeutic fluid in the reservoir to users. In one example, the fluid volume gauge may be a display of programmer 20, which displays a text and/or graphical representation of the volume of fluid in the reservoir and/or the rate at which fluid is added to or removed from the reservoir. In another example, the fluid volume gauge may be a separate display or display of another device, e.g. a laptop, desktop, or server computer, which is communicatively connected to IMD 12 and configured to display a text and/or graphical representation of the volume of fluid in the reservoir and/or the rate at which fluid is added to or removed from the reservoir.

Figure 2:
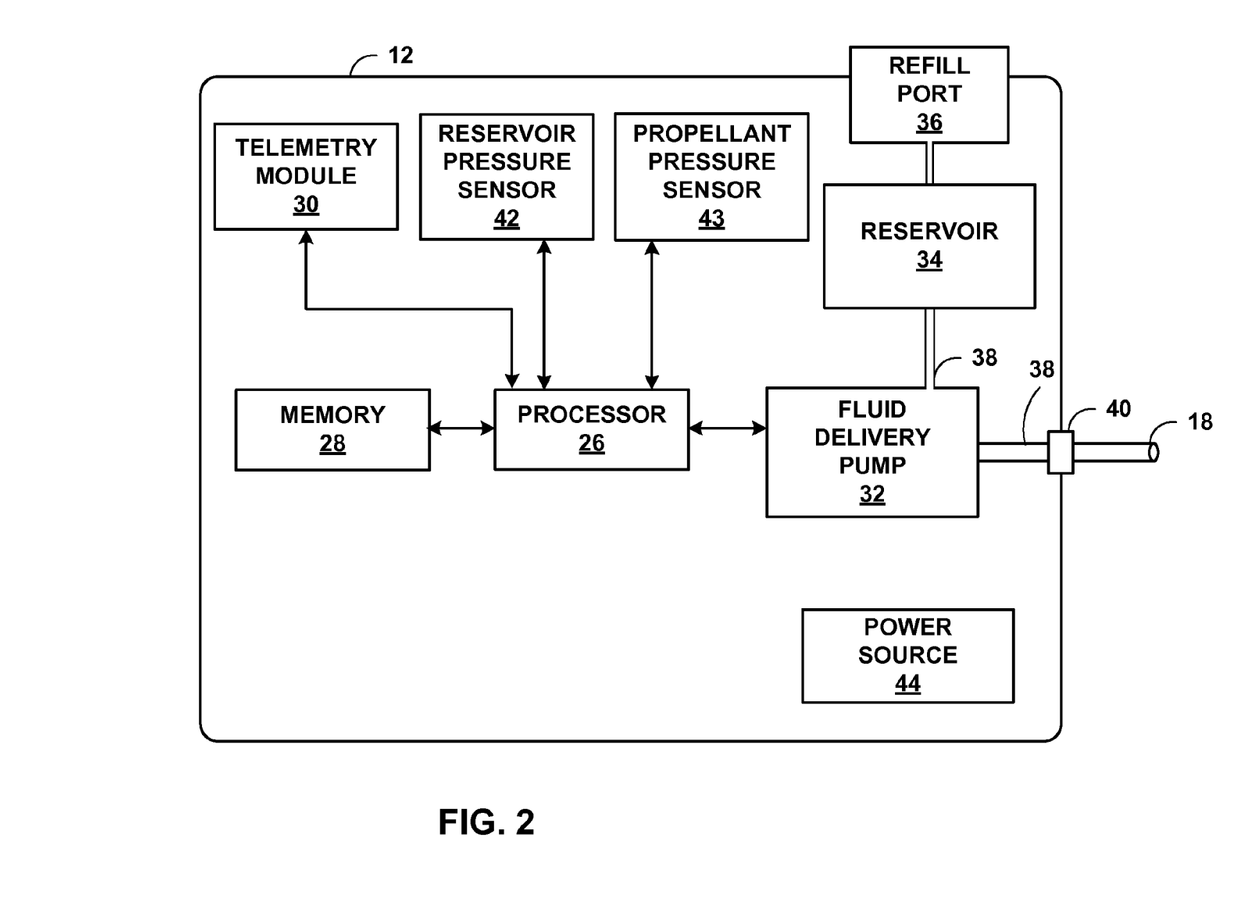
FIG. 2 is functional block diagram illustrating an example of the implantable fluid delivery device of FIG. 1.

FIG. 2 is a functional block diagram illustrating components of an example of IMD 12, which includes processor 26, memory 28, telemetry module 30, fluid delivery pump 32, reservoir 34, refill port 36, internal tubing 38, catheter access port 40, reservoir pressure sensor 42, propellant chamber pressure sensor 43, and power source 44. Processor 26 is communicatively connected to memory 28, telemetry module 30, and fluid delivery pump 32. Fluid delivery pump 32 is connected to reservoir 34 and internal tubing 38. Reservoir 34 is connected to refill port 36. Catheter access port 40 is connected to internal tubing 38 and catheter 18.

IMD 12 also includes power source 44, which is configured to deliver operating power to various components of the IMD. In some examples, IMD 12 may include a plurality of reservoirs for storing more than one type of therapeutic fluid. In some examples, IMD 12 may include a single long tube that contains the therapeutic fluid in place of a reservoir. However, for ease of description, an IMD 12 including a single reservoir 34 is primarily described with reference to the disclosed examples.

During operation of IMD 12, processor 26 controls fluid delivery pump 32 with the aid of instructions associated with program information that is stored in memory 28 to deliver a therapeutic fluid to patient 16 via catheter 18. Instructions executed by processor 26 may, for example, define therapy programs that specify the dose of therapeutic fluid that is delivered to a target tissue site within patient 16 from reservoir 30 via catheter 18. The programs may further specify a schedule of different therapeutic fluid rates and/or other parameters by which IMD 12 delivers therapy to patient 16.

In general, a therapy program stored in memory 28 and executed by processor 26 defines one or more therapeutic fluid doses to be delivered from reservoir 34 to patient 16 through catheter 18 by IMD 12. A dose of therapeutic fluid generally refers to a total amount of therapeutic fluid, e.g., measured in milligrams or other volumetric units, delivered over a total amount of time, e.g., per day or twenty-four hour period. The amount of therapeutic fluid in a dose may convey to a caregiver an indication of the probable efficacy of the fluid and the possibility of side effects.

In general, a sufficient amount of the fluid should be administered in order to have a desired therapeutic effect, such as pain relief. However, the amount of the therapeutic fluid delivered to the patient should be limited to a maximum amount, such as a maximum daily amount, in order not to avoid potential side effects. Therapy program parameters specified by a user, e.g., via programmer 20 may include fluid volume per dose, dose time period, maximum dose for a given time interval e.g., daily. In some examples, dosage may also prescribe particular concentrations of active ingredients in the therapeutic fluid delivered by IMD 12 to patient 16.

The manner in which a dose of therapeutic fluid is delivered to patient 16 by IMD 12 may also be defined in the therapy program. For example, processor 26 of IMD 12 may be programmed to deliver a dose of therapeutic fluid according to a schedule that defines different rates at which the fluid is to be delivered at different times during the dose period, e.g., a twenty-four hour period. The therapeutic fluid rate refers to the amount, e.g., in volume, of therapeutic fluid delivered over a unit period of time, which may change over the course of the day as IMD 12 delivers the dose of fluid to patient 16.

As an example, IMD 12 could be programmed to deliver therapeutic fluid to patient 16 at a rate of 20 microliters per hour. In the event the therapy program prescribes this fluid delivery rate for a twenty four hour period and assuming no patient or other boluses during the period of time, the dose of fluid delivered to patient 16 by IMD 12 will be 480 microliters (per twenty four hours). The therapy program may include other parameters, including, e.g., definitions of priming and patient boluses, as well as time intervals between successive patient boluses, sometimes referred to as lock-out intervals.

Therapy programs may be a part of a program group, where the group includes a number of therapy programs. Memory 28 of IMD 12 may store one or more therapy programs, as well as instructions defining the extent to which patient 16 may adjust therapy parameters, switch between therapy programs, or undertake other therapy adjustments. Patient 16 or a clinician may select and/or generate additional therapy programs for use by IMD 12, e.g., via external programmer 20 at any time during therapy or as designated by the clinician.

Components described as processors within IMD 12, external programmer 20, or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination.

In one example, processor 26 of IMD 12 is programmed to deliver a dose of therapeutic fluid to patient 16, which is defined in memory 28 of the device by a volume of therapeutic fluid delivered to the patient in one day. IMD 12 is also programmed according to a therapy schedule such that the fluid is delivered at different rates at different times during the day, which may be stored in memory 28, e.g., as a look-up table associating different fluid rates at different times during the day.

Upon instruction from processor 26, fluid delivery pump 32 draws fluid from reservoir 34 and pumps the fluid through internal tubing 38 to catheter 18 through which the fluid is delivered to patient 16 to effect one or more of the treatments described above in accordance with the program stored on memory 28. Internal tubing 38 is a segment of tubing or a series of cavities within IMD 12 that run from reservoir 34, around or through fluid delivery pump 32 to catheter access port (CAP) 40.

Fluid delivery pump 32 can be any mechanism that delivers a therapeutic fluid in some metered or other desired flow dosage to the therapy site within patient 16 from reservoir 30 via implanted catheter 18. In one example, fluid delivery pump 32 is a squeeze pump that squeezes internal tubing 38 in a controlled manner, e.g., such as a peristaltic pump, to progressively move fluid from reservoir 34 to the distal end of catheter 18 and then into patient 16 according to parameters specified by the therapy program stored on memory 28 and executed by processor 26.

In various examples, fluid delivery pump 32 may be an axial pump, a centrifugal pump, a pusher plate pump, a piston-driven pump, or other means for moving fluid through internal tubing 38 and catheter 18. In one example, fluid delivery pump 32 is an electromechanical pump that delivers fluid by the application of pressure generated by a piston that moves in the presence of a varying magnetic field and that is configured to draw fluid from reservoir 34 and pump the fluid through internal tubing 38 and catheter 18 to patient 16.

Generally speaking, in examples according to this disclosure, reservoir 34 includes an expandable and contractible chamber, e.g. a bellows or resilient bladder, configured to hold a therapeutic fluid that IMD 12 delivers to patient 16, e.g. according to a therapy program. The pressure of reservoir 34 may be maintained via a propellant, e.g. a propellant gas housed in a chamber surrounding the reservoir. The propellant gas chamber is separate and sealed from reservoir 34 of IMD 12. The propellant gas acts as a pressure-providing means to the chamber of reservoir 34, which modulates the pressure within the reservoir by applying pressure to the flexible structure to discharge the therapeutic fluid stored in the reservoir through internal tubing 38 to fluid delivery pump 32. In one example, the propellant gas is employed to maintain a substantially constant pressure within reservoir 34 in order to deliver the therapeutic fluid through tubing 38 to pump 32 consistently and accurately over time. Although the propellant gas is employed to maintain a substantially constant pressure within reservoir 34 for consistent deliver of the therapeutic fluid, the pressure of the gas and the reservoir may differ, as the pressure of the reservoir is also affected, e.g. by the volume of fluid in the reservoir and the resiliency of the expandable and contractible reservoir chamber, e.g. a spring constant of the bellows type reservoir. The propellant gas used to modulate the pressure of reservoir 34 of IMD 12 may be a fluid that is in phase change between a liquid state and a gas state when, e.g., in equilibrium between phases at around 35-37 degrees Celsius which is a common temperature range of the body of patient 16. The propellant gas employed in examples of IMD 12 may comprise at least one of butane, perflurohexane, or perfluropentane.

IMD 12 includes pressure sensor 42, which is configured to measure pressure in reservoir 34. Pressure sensor 42 may be arranged in a number of locations within IMD 12 including, e.g., in reservoir 34 or refill port 26. Regardless of where arranged, pressure sensor 42 is communicatively connected to processor 26, via suitable sensor electronics, to transmit pressure-related information to the processor for analysis and storage on memory 28 in order to, e.g., determine the actual rate at which therapeutic fluid is delivered from reservoir 34 to patient 16, and/or the actual volume of therapeutic fluid remaining in the reservoir.

IMD 12 also includes gas chamber pressure sensor 43, which is configured to measure pressure in a propellant gas chamber surrounding reservoir 34. Pressure sensor 43 may be arranged in a number of locations within IMD 12 and is fluidly connected to the propellant gas chamber via a fluid connection, including, e.g. tubes or cavities. Regardless of where arranged, pressure sensor 43 is communicatively connected to processor 26 to transmit pressure-related information to the processor for analysis and storage on memory 28 in order to, e.g., determine the actual rate at which therapeutic fluid is delivered from reservoir 34 to patient 16, and/or the actual volume of therapeutic fluid remaining in the reservoir.

Pressure sensors 42 and 43 may be electronically coupled to processor 26, or a processor of another device, in a variety of ways including electrical wiring (not shown) or a wireless link between the pressure sensor and the processing device. Pressure sensors 42 and 43 may each be any device capable of measuring pressure of reservoir 34. For example, each of pressure sensors 42 and 43 may be a capacitive measurement device which determines pressure by measuring the change in capacitance of a flexible membrane attached to an interior wall of, but electrically insulated from, a conductive, gas-filled cavity due to deflections caused by pressure applied over the flexible membrane (i.e., a capacitive pressure sensor). Alternatively, each of pressure sensors 42 and 43 may be a sensor that utilizes the piezo-electric effect (i.e., a piezo-electric pressure sensor) or resistive change due to metallic strain (i.e., a strain gauge pressure sensor) in order to measure pressure applied. Other types of pressure sensors not specifically described may also be employed in examples according to this disclosure.

In examples according to this disclosure, processor 26 of IMD 12, alone or in conjunction with a processor of programmer 20 or another device communicatively connected to IMD 12, may be configured to measure the pressure of reservoir 34 and propellant gas chamber 40 and estimate the volume of therapeutic fluid in the reservoir based on a pressure differential between the reservoir pressure and the propellant gas chamber pressure. In one example, processor 26 is configured to measure the pressure within reservoir 34 with pressure sensor 42. For example, processor 26 may receive measurements from pressure sensor 42 of the pressure within reservoir 34 periodically or continuously during operation of IMD 12 to deliver therapy to patient 16 and/or during refill operations, in which a clinician fills the reservoir with a therapeutic fluid. In one example, processor 26 may receive and store reservoir pressure measurements from sensor 42 in memory 28, e.g. for future analysis of reservoir pressure trends over time.

Similar to the measurement of pressure in reservoir 34, processor 26 may be configured to measure the pressure within propellant gas chamber 50 with propellant chamber pressure sensor 43. For example, processor 26 may control propellant chamber pressure sensor 43 to measure pressure within chamber 50 periodically or continuously during operation of IMD 12 to deliver therapy to patient 16 and/or during refill operations. In one example, processor 26 may receive and store propellant gas chamber pressure measurements from sensor 43 in memory 28, e.g. for future analysis of propellant gas chamber pressure trends over time.

After measuring pressure within reservoir 34 and propellant gas chamber 50 with pressure sensors 42, 43, respectively, processor 26 of IMD 12 may be configured to calculate the pressure differential between the reservoir and propellant gas chamber. For example, processor 26 may calculate the pressure differential, delta P ($\Delta P$), between the pressure within reservoir 34, $P_R$, and the pressure within propellant gas chamber 50, $P_G$, according to the following formula.

$$\Delta P = P_R - P_G \qquad (1)$$

There are a number of conditions under which IMD 12, and, in one example, processor 26 may be called on to estimate the volume of therapeutic fluid in reservoir 34. For example, processor 26 may estimate the volume of fluid in reservoir 34 as fluid delivery pump 32 delivers the fluid to patient 16, e.g. according to a therapy program stored in memory 28. In another example, processor 26 may estimate the volume of fluid in reservoir 34 as a user, e.g. a clinician adds fluid to or removes fluid from the reservoir, e.g. via refill port 36. In such examples, processor 26 may also estimate the rate at which the therapeutic fluid is added to or removed from reservoir 34. Other operating conditions of IMD 12 may also call for volume estimations according to this disclosure, including, e.g., when reservoir 34 is at least partially filled with a therapeutic fluid such that a refill operation is not necessary, but pump 32 is not currently delivering the fluid to patient 16. For example, processor 26 of IMD 12 may periodically estimate the volume of fluid in reservoir 34 between therapy delivery sessions to check that fluid has not been removed from the device, e.g. via a hypodermic needle through refill port 36 into the reservoir, since the last time the processor estimated fluid volume.

The pressure differential, $\Delta P$, between the pressure within reservoir 34, $P_R$, and the pressure within propellant gas chamber 50, $P_G$, of IMD 12 may be a function of a number of different parameters, including the volume of fluid in the reservoir. As noted above, the pressure differential between the pressure within reservoir 34 and the pressure within propellant gas chamber 50 may change proportionally with volume regardless of temperature change effects. For example, the pressure of reservoir 34 measured by pressure sensor 42 and the pressure of propellant gas chamber 50 measured by pressure sensor 43 may be affected approximately equally by temperature effects. However, only the pressure of reservoir 34 measured by pressure sensor 42 may be affected by the amount of fluid volume within the reservoir.

As such, the pressure differential between the pressure within reservoir 34 and the pressure within propellant gas chamber 50 may act to cancel the temperature effects on pressure, while retaining the volume effects. Thus, the differential pressure measurement is proportional to the volume of fluid in the reservoir of the device and this estimation of volume is substantially unaffected by temperature changes. The volume effect on the pressure differential may be a function, at least in part, of a constant that represents pressure sensitivity to volume changes. The pressure differential between the pressure within reservoir 34 and the pressure within propellant gas chamber 50 of IMD 12 may also be a function of the rate, r, at which fluid is added to or removed from the reservoir, e.g. during a refill operation. In view of the foregoing, in one example, the volume, V, of fluid in reservoir 34 of IMD 12 may be expressed according to the following relationship.

$$V = f(\Delta P, K_V, r) \qquad (2)$$

In equation (2) above, the pressure sensitivity to volume constant, $K_V$, is a characteristic of reservoir 34 of IMD 12, which behaves like a spring. For example, reservoir 34 may be formed as a resilient bellows, the spring constant or characteristic, $K_V$, of which represents the amount of incremental change in pressure in the reservoir per incremental change in volume of fluid in the reservoir. In one example, the pressure sensitivity to volume constant, $K_V$, for reservoir 34 of IMD 12 may be stored in memory 28 and retrieved by processor 26 from the memory to calculate the volume of therapeutic fluid in the reservoir. The estimation of the volume of fluid in reservoir 34, e.g. by processor 26 of IMD 12 based on the pressure differential between the pressure within reservoir 34 and the pressure within propellant gas chamber 50 of IMD 12 is described in greater detail with reference to the example IMD configuration illustrated in FIG. 3.

Figure 3:
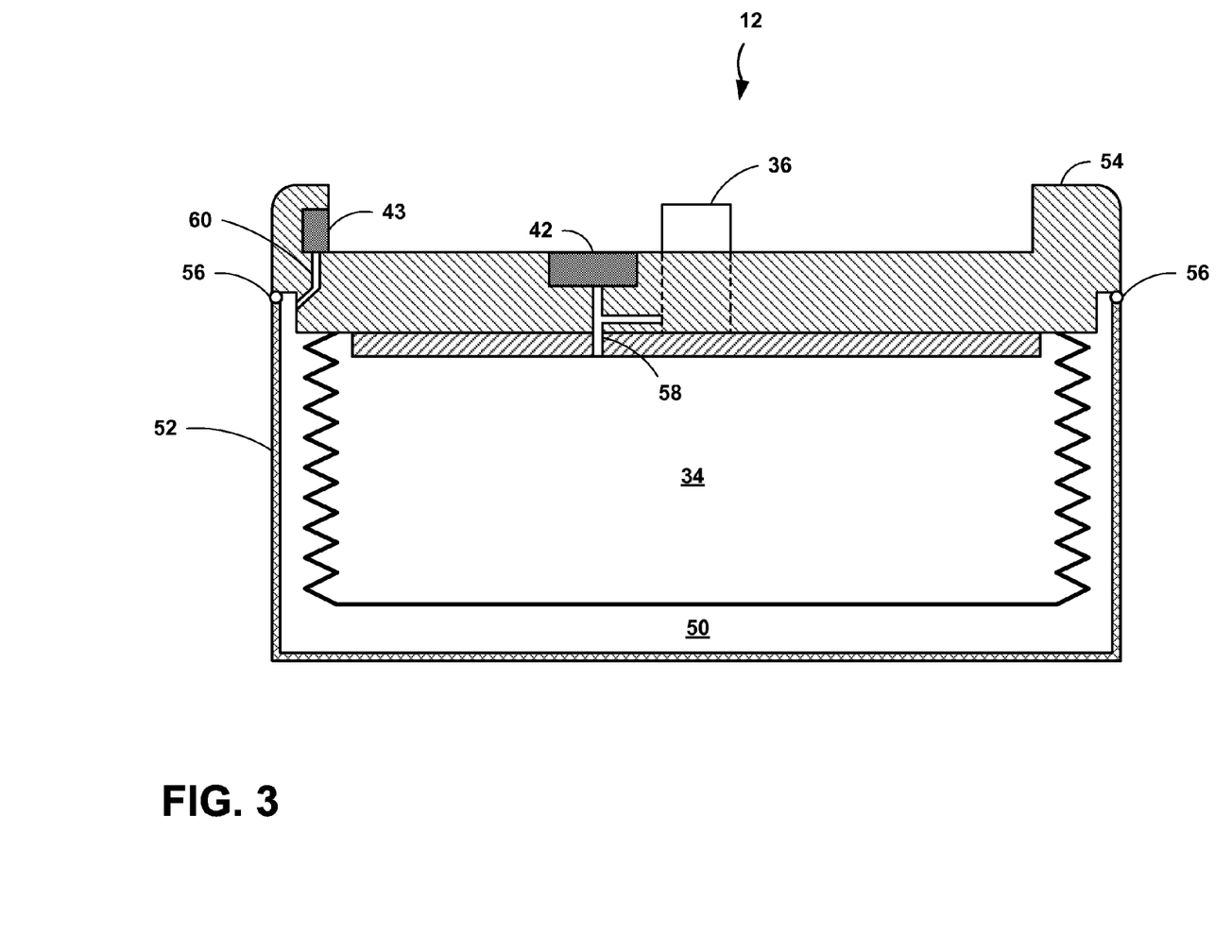
FIG. 3 is a conceptual diagram illustrating a sectional view of an example configuration of the implantable fluid delivery device of FIG. 2.

FIG. 3 is a conceptual diagram illustrating a sectional view of an example configuration of IMD 12 including reservoir pressure sensor 42 and propellant chamber pressure sensor 43. In the example of FIG. 3, IMD 12 includes reservoir 34, refill port 36, internal tubing 38, reservoir pressure sensor 42, propellant gas chamber pressure sensor 43, propellant gas chamber 50, housing shield 52, and bulkhead 54. In FIG. 3, reservoir 34 includes an expandable and contractible bellows configured to store a therapeutic fluid at a substantially constant pressure with the assistance of a propellant gas contained within chamber 50. Channel 58 connects reservoir pressure sensor 42 to reservoir 34 and to a chamber in refill port 36. Channel 60 connects propellant chamber pressure sensor 43 to propellant gas chamber 50. Bulkhead 54 is connected to housing shield 52 by weld 56.

In one example of the arrangement illustrated in FIG. 3, propellant chamber pressure sensor 43 may measure the pressure within gas propellant chamber 50 directly such that the pressure sensor reading corresponds directly to the pressure in the chamber. In other words, in one example, the pressure measured by propellant chamber pressure sensor 43, $P_{S1}$, is approximately equal to the actual pressure within gas chamber 50, $P_G$. Reservoir pressure sensor 42, however, may be positioned with respect to reservoir 34 such that the pressure measured by sensor 42, $P_{S2}$, is not only a function of the actual pressure within the reservoir, but also of a fluid restriction constant, $R_F$, of channel 58 between sensor and reservoir and the rate, r, at which a therapeutic fluid is added to or removed from the reservoir via refill port 36.

Periodically, fluid may need to be supplied percutaneously to reservoir 34 because all of a therapeutic fluid has been or will be delivered to patient 16, or because a clinician wishes to replace an existing fluid with a different fluid or similar fluid with different concentrations of therapeutic ingredients. In some examples, a therapeutic fluid may also be removed percutaneously from reservoir 34. Refill port 36 can therefore comprise a self-sealing membrane to prevent loss of therapeutic fluid delivered to reservoir 34 via refill port 36. For example, after a percutaneous delivery system, e.g., a hypodermic needle, penetrates the membrane of refill port 36, the membrane may seal shut when the needle is removed from refill port 36. The rate, r, at which fluid is added to or removed from reservoir 34 in this manner, may affect the pressure sensed by reservoir pressure sensor 42 in the example configuration of FIG. 3. The relationship between measured pressure and actual pressure of propellant gas chamber 50 and reservoir 34 may, e.g., be expressed according to the following formulas.

$$P_{S1} = P_G \tag{3}$$

$$P_{S2} = P_R + R_F r \tag{4}$$

Additionally, the actual pressure within reservoir 34, $P_R$, may be a function of the actual pressure within the propellant gas chamber 50, $P_G$, and the volume of therapeutic fluid in the reservoir. In one example, the actual pressure within reservoir 34, $P_R$, may be expressed according to the following formula.

$$P_R = P_G + K_V(V - V_o) \tag{5}$$

In the foregoing equation (5), the constant, $V_o$, is the volume of fluid in reservoir 34 when the bellows of the reservoir is in an equilibrium state. In some examples, reservoir 34 may include a bellows that acts as a spring, compressing and expanding depending on the volume of fluid in the reservoir and the pressure of the propellant gas in gas chamber 50. The bellows of reservoir 34, however, has an equilibrium state where the bellows is in an unloaded position, i.e. the spring bellows is neither compressed or expanded from the position it naturally assumes without the influence of outside forces. The volume of fluid in reservoir 34 when the bellows is in this equilibrium unloaded state is $V_o$, which is a characteristic of the reservoir that may, e.g., be stored in memory 28 of IMD 12. Substituting and simplifying formulas (3)-(5) above, an estimate of the volume of fluid in reservoir 34 of IMD 12 as a function of the measured pressure differential, $\Delta P_S$, between a pressure measured by reservoir pressure sensor 42, $P_{S2}$, and a pressure measured by propellant chamber pressure sensor 43, $P_{S1}$, may be expressed according to the following formulas.

$$\Delta P_S = P_{S2} - P_{S1} = P_G + R_F r + K_V(V - V_o) - P_G \tag{6}$$

$$\Delta P_S = R_F r + K_V(V - V_o) \tag{7}$$

$$V = \frac{\Delta P_S + K_V V_o - R_F r}{K_V} \tag{8}$$

In some examples, the rate, r, at which fluid is added to or removed from reservoir 34 via refill port 36 may not be known, as the fluid may be introduced into the reservoir by a clinician at an arbitrary rate, e.g., via a hypodermic needle. As such, in order to determine the volume of therapeutic fluid in reservoir 34 employing the relationships expressed in equation (8) further simplification may be required. In examples in which processor 26 estimates the volume of fluid in reservoir 34 as fluid delivery pump 32 delivers the fluid to patient 16, e.g. according to a therapy program stored in memory 28 and fluid is not being added to or removed from the reservoir via refill port 36, the rate term simply drops out of equation (8). In other words, in the event fluid is not being added to or removed from reservoir 34 via refill port 36, processor 26 may calculate the volume, V, of therapeutic fluid in the reservoir based on the measured pressure differential between the measured pressure within reservoir 34 and the measured pressure within propellant gas chamber 50 according to the following formulas.

$$V = \frac{\Delta P_S + K_V V_o - 0}{K_V} \tag{9}$$

$$V = \frac{\Delta P_S}{K_V} + V_o \tag{10}$$

In examples in which fluid is being added to or removed from reservoir 34 via refill port 36, e.g. during a refill operation, however, the rate, r, at which the fluid is added or removed does not drop out of equation (8). In such cases, the volume of therapeutic fluid in reservoir 34 of IMD 12 may need to be estimated in a different manner than by direct calculation as a function of the measured pressure differential, $\Delta P_S$, and the pressure sensitivity to volume constant, $K_V$, as shown in equation (10). In one such example, the volume of therapeutic fluid in reservoir 34 of IMD 12 may be estimated by first estimating the rate, r, at which fluid is being added to or removed from the reservoir as a function of the measured pressure differential and then calculating the volume of fluid added or removed by multiplying the rate by the time, t, over which the fluid is added or removed. This may be accomplished, e.g., by processor 26 taking the first derivative of equation (8) with respect to time as shown in the following formula.

$$\frac{\Delta V}{\Delta t} = \frac{1}{K_V}\left(\frac{\Delta(\Delta P_S)}{\Delta t}\right) + \frac{\Delta}{\Delta t}\left(\frac{K_V \times V_o}{K_V}\right) - \frac{R_F}{K_V}\left(\frac{\Delta r}{\Delta t}\right) \tag{11}$$

In the foregoing formula, the first derivative of the volume, $\Delta V/\Delta t$, of fluid in reservoir 34 with respect to time is equated to a number of terms including the first derivative of the measured pressure differential, $\Delta(\Delta P_S)/\Delta t$, between the measured pressure within reservoir 34 and the measured pressure within propellant gas chamber 50 with respect to time. The first derivative of the measured pressure differential, $\Delta(\Delta P_S)/\Delta t$, between the measured pressure within reservoir 34 and the measured pressure within propellant gas chamber 50 with respect to time is equal to the time rate of change of the measure pressure differential, $\Delta P_S$. Thus, in one example, the first derivative of the measured pressure differential, $\Delta(\Delta P_S)/\Delta t$, may be equal to the difference between the pressure differential, $\Delta P_{S,t=1\_2}$, between the pressure, $P_{S1,t=1}$, within reservoir 34 measured by pressure sensor 42 and the pressure, $PS_{2,t=1}$, within propellant gas chamber 50 measured by pressure sensor 43 at a first time instant and the pressure differential, $\Delta P_{S,t=2}$, between the pressure, $P_{S1,t=2}$, within reservoir 34 measured by pressure sensor 42 and the pressure, $P_{S2,t=2}$, within propellant gas chamber 50 measured by pressure sensor 43 at a second time instant after the first time instant.

By assuming that the fluid is added to or removed from reservoir 34 at a constant rate, r, the first term in equation (11) goes to zero, because the first derivative of the rate, $\Delta r/\Delta t$, at which fluid is added to or removed from the reservoir with respect to time is zero. Additionally, the first derivative of the constant $V_o$ corresponding to the volume of fluid in reservoir 34 when the bellows is in an equilibrium state is also equal to zero. In such an example, therefore, the rate of change of the measured pressure differential is proportional to the rate of change of the volume of fluid in reservoir 34. In one example, processor 26 may estimate the rate of change of the volume of fluid in reservoir 34 over time based on the measured pressure differential according to the following formula.

$$\frac{\Delta V}{\Delta t} = \frac{1}{K_V}\left(\frac{\Delta(\Delta P_S)}{\Delta t}\right) \quad (12)$$

The rate of change of the volume of fluid in reservoir 34 with respect to time, $\Delta V/\Delta t$, is the rate, r, at which the fluid is added to or removed from the reservoir. As such, processor 26 may estimate, e.g. during a refill operation, the rate, r, at which the fluid is added to or removed from reservoir 34 based on the measured pressure differential and the pressure sensitivity to volume constant for IMD 12 according to the following equation.

$$r = \frac{1}{K_V}\left(\frac{\Delta(\Delta P_S)}{\Delta t}\right) \quad (13)$$

Additional information regarding and techniques for estimating the rate at which a therapeutic fluid is added to or removed from a reservoir of an IMD based on pressure is described in U.S. patent application Ser. No. 12/619,145, filed Nov. 16, 2009 and entitled "PRESSURE BASED REFILL STATUS MONITOR FOR IMPLANTABLE PUMPS," the entire content of which is incorporated herein by reference.

Referring again to equation (13), processor 26 may also estimate the change in volume, $\Delta V/\Delta t$, of fluid in reservoir 34 as fluid is added to or removed from the reservoir by multiplying equation (13) by the amount of time, $\Delta t$, over which fluid is added or removed. In such an example, processor 26 may estimate the absolute volume of fluid in reservoir 34 by adding the change in volume of fluid in the reservoir to a starting volume, $V_{start}$, e.g. the volume of fluid in the reservoir when the refill operation started. As such, processor 26 may estimate the volume of fluid in reservoir 34 as a function of the measured pressure differential according to the following formulas.

$$\Delta V = \frac{\Delta(\Delta P_S)}{K_V} \quad (14)$$

$$V = V_{start} + \Delta V \quad (15)$$

$$V = \frac{\Delta(\Delta P_S)}{K_V} + V_{start} \quad (16)$$

Thus, in examples according to this disclosure, IMD 12, e.g. processor 26 may be configured to estimate the volume of therapeutic fluid in reservoir 34 based on a measured pressure differential equal to the difference between the pressure within the reservoir measured by reservoir pressure sensor 42 and the pressure within gas propellant chamber 50 measured by gas chamber pressure sensor 43. In one example, processor 26 is configured to estimate the volume of therapeutic fluid in reservoir 34 based on the measured pressure differential during delivery of the fluid to patient 16 by the IMD via catheter 18 according to equation (10). In such an example, processor 26 may retrieve values of the pressure sensitivity to volume constant, $K_V$, and the volume, $V_o$, of fluid in reservoir 34 when the bellows of the reservoir is in an equilibrium state, both of which may be constants that are characteristics of the bellows of reservoir 34 of IMD 12, from memory 28 and receive signals from reservoir pressure sensor 42 and gas chamber pressure sensor 43 to estimate the volume of fluid in the reservoir during therapeutic fluid delivery according to equation (10).

In another example, processor 26 is configured to estimate the volume of therapeutic fluid in reservoir 34 based on the measured pressure differential fluid is being added to or removed from the reservoir via refill port 36 according to equation (16). In such an example, processor 26 may retrieve a value of $K_V$, which is a constant that is a characteristic of the bellows of reservoir 34 of IMD 12, from memory 28. Additionally, processor 26, some time prior to fluid being added to or removed from reservoir 34 via refill port 36, may estimate the volume of fluid in the reservoir and may store the value for use as the starting volume, $V_{start}$. As fluid is being added to or removed from reservoir 34 via refill port 36, processor 26 may then may retrieve values of $K_V$ and $V_{start}$ and receive signals from reservoir pressure sensor 42 and gas chamber pressure sensor 43 to estimate the volume of fluid in the reservoir, e.g. during a refill operation according to equation (16).

Additionally, in another example, processor 26 is configured to estimate the rate, r, at which fluid is added to or removed from reservoir 34 via refill port 36, e.g. during a refill operation according to equation (13). In such an example, processor 26 may retrieve a value of $K_V$, which is a constant that is a characteristic of the bellows of reservoir 34 of IMD 12, from memory 28. In this example, processor 26, or some other software or hardware component(s) of IMD 12 may track the time, t, over which fluid is added to or removed from reservoir 34 via refill port 36. As fluid is being added to or removed from reservoir 34 via refill port 36, processor 26 may retrieve the value of $K_V$ and receive signals from reservoir pressure sensor 42 and gas chamber pressure sensor 43. Processor 26 may determine the change in the measured pressure differential based on different signals received from reservoir pressure sensor 42 and gas chamber pressure sensor 43 over a period of time, $\Delta t$, from which the processor may then estimate the rate at which fluid is added to or removed from reservoir 34, e.g. during a refill operation according to equation (13).

Processor 26 of IMD 12 may also be configured to control a number of indicators related to the fluid in reservoir 34 of IMD 12. For example, processor 26 may be configured to control a volume gauge to indicate to patient 16 or another user the volume of therapeutic fluid in reservoir 34 as the IMD delivers therapy to the patient. Processor 26 may also be configured to control a volume gauge to indicate to patient 16 and/or another user, e.g. a clinician the volume of therapeutic fluid in reservoir 34 as fluid is added to or removed from the reservoir via refill port 36. In one example, processor 26 is configured to control an indicator of the rate at which fluid is added to or removed from reservoir 34 via refill port 36, e.g. during a refill operation performed by a clinician.

The indicators processor 26 is configured to control related to the therapeutic fluid in reservoir 34 of IMD 12 may include a variety of forms. For example, a fluid volume gauge controlled by processor 26 may include presenting information on a display of programmer 20, which may, e.g., display a text or graphical representation of the volume of fluid in the reservoir. In another example, processor 26 may include presenting the fluid volume gauge or other indicator on a separate display or display of another device, e.g. a laptop, desktop, or server computer, which is communicatively connected to IMD 12 and configured to display a text or graphical representation of the volume of fluid in the reservoir.

Processor 26 may also trigger one or more actions based on the about the therapeutic fluid in reservoir 34 derived from the measured pressure differential between a pressure measured by reservoir pressure sensor 42 and a pressure measured by propellant chamber pressure sensor 43 including generation of an empty or full reservoir alarm or displaying the fill status of reservoir 34 on an external device including, e.g., programmer 20 by transmitting reservoir volume and/or fill status information to the programmer via telemetry module 30. Alarms triggered by processor 26, or another component of IMD 12 or another device, e.g. programmer 20, may generally include audible, tactile, and/or visual alerts. For example, a reservoir empty or full state alarm may include audible alerts issued by programmer 20 or another external device associated with therapy system 10. In another example, a reservoir fill status alarm includes IMD 12 vibrating within the body of patient 16, thereby providing a tactile alert. In other examples, the alarm includes text or graphical messages delivered to patient 16 and/or a clinician via text message or e-mail from programmer 20 or another electronic device communicatively connected to IMD 12 and/or programmer 20, thereby providing a visual alert.

In one example, processor 26 may also trigger an alarm related to the rate at which a user, e.g. a clinician is adding fluid to or removing fluid from reservoir 34, e.g. during a refill operation. Various protocols may be recommended for refill operations for IMD 12. For example, a maximum refill rate may be recommended for IMD 12 to reduce the risk that a clinician will overfill reservoir 34, which may result in causing one or more components of the IMD to malfunction, e.g. pressure locking reservoir 34 and thereby inhibiting or preventing proper delivery of therapeutic fluid from the reservoir to patient 16. In such an example, processor 26 may trigger an alarm in the event the rate at which a clinician adds fluid to reservoir 34 is estimated based on the measured pressure differential between a pressure measured by reservoir pressure sensor 42 and a pressure measured by propellant chamber pressure sensor 43 to be greater than or equal to the maximum recommended refill rate. Processor 26 may simply sound or issue an alert to the clinician to slow down the refill rate, or may, in one example, indicate to the clinician, e.g. via a display of programmer 20 the rate at which they are currently filling and how much they should slow down the refill to come into compliance with the recommended maximum. In this manner, the clinician may receive closed loop feedback as to filling state while the clinician is filling reservoir 34.

Referring again to FIG. 2, memory 28 of IMD 12 stores program instructions and related data that, when executed by processor 26, cause IMD 12 and processor 26 to perform the functions attributed to them in this disclosure. For example, memory 28 of IMD 12 may store instructions for execution by processor 26 including, e.g., therapy programs, programs for monitoring the volume of therapeutic fluid in reservoir 34, and any other information regarding therapy delivered to patient 16 and/or the operation of IMD 12. Memory 28 may include separate memories for storing instructions, patient information, therapy parameters, therapy adjustment information, program histories, and other categories of information such as any other data that may benefit from separate physical memory modules. Therapy adjustment information may include information relating to timing, frequency, rates and amounts of patient boluses or other permitted patient modifications to therapy.

At various times during the operation of IMD 12 to treat patient 16, communication to and from IMD 12 may be necessary to, e.g., change therapy programs, adjust parameters within one or more programs, configure or adjust a particular bolus, or to otherwise download information to or from IMD 12. Processor 26 controls telemetry module 30 to wirelessly communicate between IMD 12 and other devices including, e.g. programmer 20. Telemetry module 30 in IMD 12, as well as telemetry modules in other devices described in this disclosure, such as programmer 20, can be configured to use RF communication techniques to wirelessly send and receive information to and from other devices respectively according to, e.g., the 802.11 or Bluetooth specification sets, infrared (IR) communication according to the IRDA specification set, or other standard or proprietary telemetry protocols. In addition, telemetry module 30 may communicate with programmer 20 via proximal inductive interaction between IMD 12 and the external programmer. Telemetry module 30 may send information to external programmer 20 on a continuous basis, at periodic intervals, or upon request from the programmer.

Power source 44 delivers operating power to various components of IMD 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As another alternative, an external inductive power supply could transcutaneously power IMD 12 as needed or desired.

Figure 4:
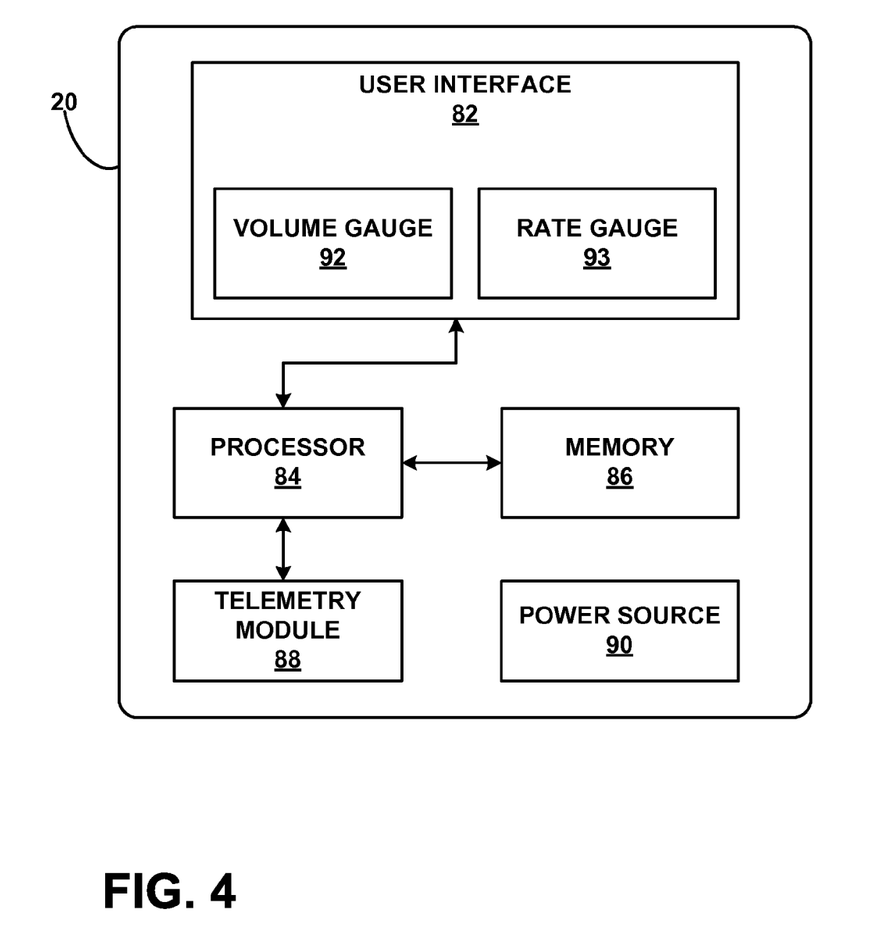
FIG. 4 is a functional block diagram illustrating an example of the external programmer of FIG. 1.

FIG. 4 is a functional block diagram illustrating an example of various components of external programmer 20 for IMD 12. As shown in FIG. 4, external programmer 20 may include user interface 82, processor 84, memory 86, telemetry module 88, and power source 90. A clinician or patient 16 interacts with user interface 82 in order to manually change the parameters of a therapy program, change therapy programs within a group of programs, view therapy information, view historical or establish new therapy programs, or otherwise communicate with IMD 12 or view or edit programming information. Processor 84 controls user interface 82, retrieves data from memory 86 and stores data within memory 86. Processor 84 also controls the transmission of data through telemetry module 88 to IMD 12. The transmitted data may include therapy program information specifying various therapeutic fluid delivery parameters. Memory 86 may store, e.g., operational instructions for processor 84 and data related to therapy for patient 16.

Programmer 20 may be a hand-held computing device that includes user interface 82 that can be used to provide input to programmer 20. For example, programmer 20 may include a display screen that presents information to the user and a keypad, buttons, a peripheral pointing device, touch screen, voice recognition, or another input mechanism that allows the user to navigate though the user interface of programmer 20 and provide input. In other examples, rather than being a handheld computing device or a dedicated computing device, programmer 20 may be a larger workstation or a separate application within another multi-function device.

User interface 82 may generally include a display screen or other output mechanisms and buttons or other input mechanisms that allow a user to receive information from and provide input to external programmer 20, respectively. In one example, user interface includes one or more of a touch pad, increase and decrease buttons, an emergency shut off button, and other buttons needed to control the therapy delivered to patient 16 by IMD 12. In another example, user interface 82 may additionally or only utilize a touch screen display including, e.g., a liquid crystal display (LCD), dot matrix display, organic light-emitting diode (OLED) display, touch screen, or any other device capable of delivering and/or accepting information. For visible indications of therapy program parameters or operational status, a display screen may suffice. For audible and/or tactile indications of therapy program parameters or operational status, programmer 20 may further include one or more audio speakers, voice synthesizer chips, piezoelectric buzzers, or the like.

User interface 82 may be configured to present therapy program information to the user as graphical bar graphs or charts, numerical spread sheets, or in any other manner in which information may be displayed. Further, user interface 82 may present nominal or suggested therapy parameters that the user may accept via user interface 82. User interface 82 also provides input mechanisms to enable the user to program IMD 12 in accordance with one or more therapy programs or otherwise provide data to IMD 12 necessary for delivering therapy to patient 16.

When programmer 20 is configured for use by a clinician, user interface 82 may be used to transmit initial programming information to IMD 12 including hardware information for system 10, e.g. the type of catheter 18, the position of catheter 18 within patient 16, a baseline orientation of at least a portion of IMD 12 relative to a reference point, and software information related to therapy delivery and operation of IMD 12, e.g. therapy parameters of therapy programs stored within IMD 12 or within programmer 20, the type and amount, e.g., by volume of therapeutic fluid(s) delivered by IMD 12 and any other information the clinician desires to program into IMD 12. The clinician may use programmer 20 during a programming session to define one or more therapy programs by which IMD 12 delivers therapy to patient 16, in which case patient 16 may provide feedback to the clinician during the programming session as to efficacy of a program being evaluated or desired modifications to the program. Programmer 20 may assist the clinician in the creation/identification of therapy programs by providing a methodical system of identifying potentially beneficial therapy parameters.

Programmer 20 may also be configured for use by patient 16. When configured as a patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 need to be replaced or recharged.

In the example of FIG. 4, user interface 82 of programmer 20, whether employed as a patient or clinician programmer, includes volume gauge 92 and rate gauge 93, which is configured to respectively indicate the volume of therapeutic fluid in reservoir 34 of IMD 12 and, under certain circumstances, the rate at which a fluid is added to or removed from the reservoir. Whether controlled by processor 26 of IMD 12, as described above, or processor 84 of programmer 20, volume gauge 92 is configured to display via user interface 82 the volume of therapeutic fluid in reservoir 34 that is determined based on the measured pressure differential between a pressure measured by reservoir pressure sensor 42 and a pressure measured by propellant chamber pressure sensor 43. Volume gauge 92 may include any combination of text or graphical representations of the volume of fluid in reservoir 34. For example, volume gauge 92 may include an iconic representation of the volume of therapeutic fluid in reservoir 34 including a series of bars that are colored, filled in, highlighted, increase and decrease in size, or otherwise vary based on the volume fluid in the reservoir. In another example, volume gauge 92 includes a graphical representation of the circular face of a mechanical gauge with numerical or other indications of the level of fluid in reservoir 34. In another example, volume gauge 92 includes a numerical or textual indication of the amount of fluid in reservoir 34.

Processor 84 of programmer 20 may be employed, in conjunction with or in lieu of processor 26 of IMD 12, to estimate the volume of therapeutic fluid in reservoir 34 based on the measured pressure differential between a pressure measured by reservoir pressure sensor 42 and a pressure measured by propellant chamber pressure sensor 43 in a manner substantially similar to that described above with reference to processor 26 of IMD 12. For example, IMD 12 may transmit measurements of the pressure of reservoir 34 and propellant gas chamber 50 measured by reservoir pressure sensor 42 and gas chamber pressure sensor 43, respectively, to programmer 20 via telemetry modules 30 and 82 of IMD 12 and programmer 20, respectively. Processor 84 may then employ the measured pressures of reservoir 34 and propellant gas chamber 50 to estimate the volume of therapeutic fluid in the reservoir and/or the rate at which fluid is added to or removed from the reservoir, e.g. during a refill operation. Additionally, processor 26 of IMD 12 may collect and store pressure measurements made by reservoir pressure sensor 42 and gas chamber pressure sensor 43 in memory 28. An external instrument, e.g. a patient programmer may automatically pull the pressure measurements from memory 28 via telemetry modules 30 and 82 on a regular basis. In one example, processor 86 may store pressure measurements made by reservoir pressure sensor 42 and gas chamber pressure sensor 43 in memory 86 and may employ the measured pressures to estimate the volume of therapeutic fluid in reservoir 34 of IMD 12 and/or the rate at which a therapeutic fluid is added to or removed from the reservoir.

Additionally, processor 84 of programmer 20 may be employed, in conjunction with or in lieu of processor 26 of IMD 12, to estimate the volume of therapeutic fluid in reservoir 34 and to control fluid volume gauge 92 of user interface 82 to indicate the estimated volume of fluid in reservoir 34. In some examples, processor 26 of IMD 12 estimates the volume of therapeutic fluid in reservoir 34 and transmits the estimated volume via telemetry module 30 to programmer 20. Processor 84 of programmer 20 may store the volume in memory 86. In other examples, however, processor 84 may query IMD 12 via telemetry module 88 to retrieve pressure measurements of reservoir 34 and propellant gas chamber 50 made by reservoir pressure sensor 42 and gas chamber pressure sensor 43, respectively, then estimate the volume of therapeutic fluid in the reservoir based the pressure differential between the two measured pressures. In either case, processor 84 of programmer 20 may store the estimated volume in memory 86. In one example, as described above, volume gauge 92 is displayed on user interface 82 of programmer 20 in the form of a text or graphical representation of the volume of fluid in the reservoir. In another example, however, a fluid volume gauge may be a separate display or display of another device, e.g. a laptop, desktop, or server computer, which is communicatively connected to programmer 20 and configured to display a text or graphical representation of the volume of fluid in reservoir 34 of IMD 12.

In one example, processor 84 of programmer 20 may also be employed, in conjunction with or in lieu of processor 26 of IMD 12, in a similar manner to that described with reference to volume estimations, to estimate the rate at which a therapeutic fluid is added to or removed from reservoir 34 and to control rate gauge 93 of user interface 82 to indicate the estimated rate at which the fluid is added to or removed from the reservoir.

Telemetry module 88 allows the transfer of data to and from programmer 20 and IMD 12, as well as other devices, e.g. according to the RF communication techniques described above with reference to FIG. 2. Telemetry module 88 may communicate automatically with IMD 12 at a scheduled time or when the telemetry module detects the proximity of IMD 12. Alternatively, telemetry module 88 may communicate with IMD 12 when signaled by a user through user interface 82. To support RF communication, telemetry module 88 may include appropriate electronic components, such as amplifiers, filters, mixers, encoders, decoders, and the like. Programmer 20 may also communicate with another programmer or computing device via a wired or wireless connection using any of a variety of communication techniques, and/or via exchange of removable media, including, e.g., magnetic or optical disks, or memory cards or sticks including, e.g., non-volatile memory. Further, programmer 20 may communicate with IMD 12 or another device via, e.g., a local area network (LAN), wide area network (WAN), public switched telephone network (PSTN), or cellular telephone network, or any other terrestrial or satellite network appropriate for use with programmer 20 and IMD 12.

Power source 90 may be a rechargeable battery, such as a lithium ion or nickel metal hydride battery. Other rechargeable or conventional primary cell batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 12 in addition to programming IMD 12. Alternatively, a recharging device may be capable of communication with IMD 12. Then, the recharging device may be able to transfer programming information, data, or any other information described herein to IMD 12. In this manner, the recharging device may be able to act as an intermediary communication device between external programmer 20 and IMD 12.

Figure 5:
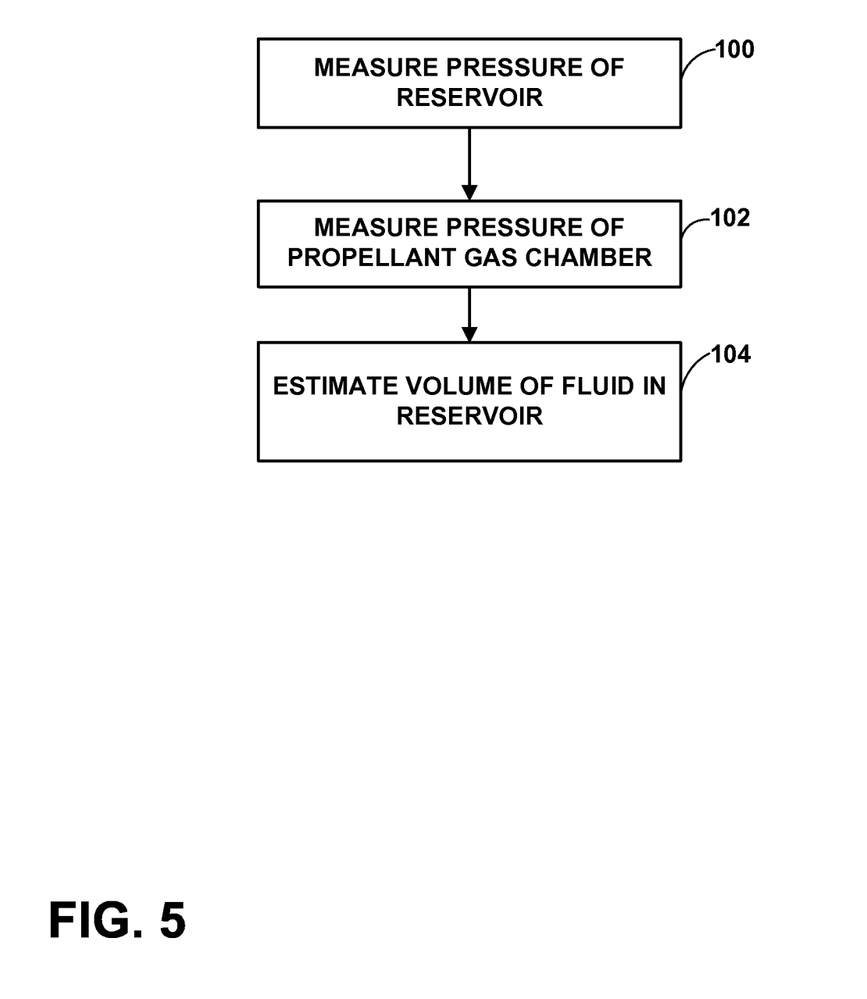
FIG. 5 is a flow diagram illustrating an example method of estimating the volume of fluid in the reservoir of a fluid delivery device.

FIG. 5 is a flow diagram illustrating an example method, which may be employed, e.g., to estimate the volume of therapeutic fluid in a reservoir of an IMD. The example method of FIG. 5 includes measuring a pressure within a reservoir of an implantable fluid delivery device (100), measuring a pressure within a propellant gas chamber of the fluid delivery device (102), and estimating a volume of a therapeutic fluid within the reservoir based on a pressure differential between the measured pressure within the reservoir and the measured pressure within the propellant gas chamber (104).

The example method of FIG. 5 is described in greater detail below with reference to IMD 12 of FIGS. 1-3. However, methods in accordance with the techniques described in this disclosure may be equally applicable to other medical devices including, e.g., a fluid delivery device including multiple reservoirs and multiple pressure sensors. Additionally, although the functions associated with the method of FIG. 5 are generally described as executed by processor 26 of IMD 12 and supported by data stored in or retrieved from memory 28, in other examples, a processor and a memory of a different device, e.g. processor 84 and memory 86 of programmer 20, may be employed instead of or in conjunction with processor 26 and memory 28 to execute one or more of the described functions.

The method of FIG. 5 includes measuring a pressure within a reservoir of an implantable fluid delivery device (100). As explained above with reference to FIGS. 2 and 3, reservoir pressure sensor 42 may be arranged, generally speaking, to measure the pressure in reservoir 34 of IMD 12. There are a number of conditions under which IMD 12, and, in one example, processor 26 may be called on to estimate the volume of therapeutic fluid in reservoir 34 and such conditions may affect the pressure measurement executed by reservoir pressure sensor 42. In one example, processor 26 may estimate the volume of fluid in reservoir 34 as fluid delivery pump 32 delivers the fluid to patient 16 and when fluid is not being added to or removed from the reservoir, in which case the pressure measurement by reservoir pressure sensor 42 is unaffected by a rate at which the fluid is added or removed.

In another example, processor 26 may estimate the volume of fluid in reservoir 34 as a user, e.g. a clinician adds fluid to or removes fluid from the reservoir, e.g. via refill port 36, in which case the pressure measured by pressure sensor 42 may be a function of the rate at which the therapeutic fluid is added or removed.

In addition to measuring a pressure within a reservoir of an implantable fluid delivery device (100), the method of FIG. 5 includes measuring a pressure within a propellant gas chamber of the fluid delivery device (102). In one example of the arrangement illustrated in FIG. 3, propellant chamber pressure sensor 43 may measure the pressure within gas propellant chamber 50 directly such that the pressure sensor reading corresponds directly to the pressure in the chamber. In other words, in one example, the pressure measured by propellant chamber pressure sensor 43, $P_{S1}$, is approximately equal to the actual pressure within gas chamber 50, $P_G$.

The method of FIG. 5 also includes estimating a volume of a therapeutic fluid within the reservoir of an IMD based on a pressure differential between the measured pressure within the reservoir and the measured pressure within the propellant gas chamber (104). In one example, processor 26 estimates the volume of fluid in reservoir 34 of IMD 12 based on a measured pressure differential between a pressure measured by reservoir pressure sensor 42 and a pressure measured by propellant chamber pressure sensor 43. The manner in which processor 26 of IMD 12 estimates the volume of fluid in reservoir 34 may be affected by, among other factors, whether or not fluid is being added to or removed from the reservoir, e.g. during a refill operation.

In one example, processor 26 may estimate the volume of fluid in reservoir 34 as fluid delivery pump 32 delivers the fluid to patient 16 and when fluid is not being added to or removed from the reservoir. In one such an example, processor 26 may calculate the volume of therapeutic fluid in reservoir 34 based on the measured pressure differential between the pressure within reservoir 34 and the pressure within propellant gas chamber 50, as well as characteristics of IMD 12 including a baseline volume of fluid in the reservoir. In one example, processor 26 may calculate the volume of therapeutic fluid in reservoir 34 according to equation (10) explained above and which is reproduced here for convenience.

$$V = \frac{\Delta P_S}{K_V} + V_o \qquad (10)$$

In the foregoing equation (10), the baseline volume, $V_o$, represents the volume of fluid in reservoir 34 when the bellows of the reservoir is in a substantially unloaded equilibrium state. The volume of fluid in reservoir 34 when the bellows is in this equilibrium unloaded state is $V_o$, which is a characteristic of the reservoir that may, e.g., be stored in memory 28 of IMD 12 and retrieved therefrom by processor 26 to estimate the volume of fluid in the reservoir. Additionally, the pressure sensitivity to volume constant, $K_v$, in equation (10) is a characteristic of reservoir 34 of IMD 12, which behaves like a spring. For example, reservoir 34 may be formed as a resilient bellows, the spring constant or characteristic, $K_v$, of which represents the amount of incremental change in pressure in the reservoir per incremental change in volume of fluid in the reservoir. In one example, the pressure sensitivity to volume constant, $K_v$, for reservoir 34 of IMD 12 may be stored in memory 28 and retrieved by processor 26 from the memory to calculate the volume of therapeutic fluid in the reservoir.

In another example of estimating a volume of a therapeutic fluid within the reservoir of an IMD based on a pressure differential between the measured pressure within the reservoir and the measured pressure within the propellant gas chamber (104), processor 26 may estimate the volume as a user, e.g. a clinician, adds fluid to or removes fluid from reservoir 34, e.g. via refill port 36 during a refill operation. In such cases, processor 26 may need to estimate the rate at which the fluid is added to or removed from reservoir 34 in order to estimate the volume of fluid in the reservoir. Additionally, processor 26 may need a baseline volume of therapeutic fluid in reservoir 34, e.g. a starting volume of fluid in the reservoir when the fluid is first added or removed.

In one example, the rate, r, at which fluid is added to or removed from reservoir 34 may be estimated by processor 26 taking the first derivative of equation (8) with respect to time as shown in the equation (11) explained above and reproduced here for convenience.

$$\frac{\Delta V}{\Delta t} = \frac{1}{K_V}\left(\frac{\Delta(\Delta P_S)}{\Delta t}\right) + \frac{\Delta}{\Delta t}\left(\frac{K_V \times V_o}{K_V}\right) - \frac{R_F}{K_V}\left(\frac{\Delta r}{\Delta t}\right) \qquad (11)$$

By assuming that the fluid is added to or removed from reservoir 34 at a constant rate, r, the first term in equation (11) goes to zero, because the first derivative of the rate, $\Delta r/\Delta t$, at which fluid is added to or removed from the reservoir with respect to time is zero. Additionally, the first derivative of the constant $V_o$ corresponding to the volume of fluid in reservoir 34 when the bellows is in an equilibrium state is also equal to zero. In such an example, therefore, the rate of change of the measured pressure differential with respect to time, $\Delta(\Delta P_S)/\Delta t$, is proportional to the rate of change of the volume of fluid in reservoir 34. The rate of change of the volume of fluid in reservoir 34 with respect to time, $\Delta V/\Delta t$, is the rate, r, at which the fluid is added to or removed from the reservoir. As such, processor 26 may estimate, e.g. during a refill operation, the rate, r, at which the fluid is added to or removed from reservoir 34 based on the measured pressure differential and the pressure sensitivity to volume constant for IMD 12 according to the following equation.

$$r = \frac{1}{K_V}\left(\frac{\Delta(\Delta P_S)}{\Delta t}\right) \qquad (13)$$

Additionally, processor 26 may also estimate the change in volume, $\Delta V/\Delta t$, of fluid in reservoir 34 as fluid is added to or removed from the reservoir by multiplying equation (13) by the amount of time, $\Delta t$, over which fluid is added or removed. In such an example, processor 26 may estimate the absolute volume of fluid in reservoir 34 (104) in accordance with the example method of FIG. 5 by adding the change in volume of fluid in the reservoir to a starting volume, $V_{start}$, e.g. the volume of fluid in the reservoir when the refill operation started. As such, processor 26 may estimate the volume of fluid in reservoir 34 as a function of the measured pressure differential (104) according to equation 16 explained above and reproduced here for convenience.

$$V = \frac{\Delta(\Delta P_S)}{K_V} + V_{start} \qquad (16)$$

In some examples, the method of FIG. 5 may include additional functions, including displaying one or more indications of the estimated volume and/or the rate at which a fluid is added to or removed from reservoir 34 and generating an alert based on the estimated volume of the therapeutic fluid within the reservoir. For example, processor 26 may cause the volume of fluid in reservoir 34 or the fill state as empty, filling, or full, to be displayed by an external display device, e.g. user interface 82 of programmer 20. Additionally, processor 26 may cause the rate at which a fluid is added to or removed from reservoir 34, e.g. during a refill operation to be displayed by an external display device, e.g. user interface 82 of programmer 20.

In one example, processor 26 of IMD 12 or processor 84 of programmer 20 may control volume gauge 92 and rate gauge 93 of user interface 82 of programmer 20 to indicate the volume of therapeutic fluid in reservoir 34 of IMD 12 and, under certain circumstances, the rate at which a fluid is added to or removed from the reservoir, respectively. Volume gauge 92 and/or rate gauge 93 may include any combination of text or graphical representations of the volume of fluid in reservoir 34. For example, volume gauge 92 may include an iconic representation of the volume of therapeutic fluid in reservoir 34 including a series of bars that are colored, filled in, highlighted, increase and decrease in size, or otherwise vary based on the volume fluid in the reservoir. In another example, volume gauge 92 includes a graphical representation of the circular face of a mechanical gauge with numerical or other indications of the level of fluid in reservoir 34. In another example, volume gauge 92 includes a numerical or textual indication of the amount of fluid in reservoir 34. Example graphical displays of the fill status of a reservoir of an IMD similar to the reservoir 34 of IMD 12 described in this disclosure are provided in related U.S. patent application Ser. No. 12/619,145, entitled "PRESSURE BASED REFILL STATUS MONITOR FOR IMPLANTABLE PUMPS," filed Nov. 16, 2009, the entire content of which is incorporated herein by this reference.

In some examples, the example method of FIG. 5 may include generating an alert based on the estimated volume of the therapeutic fluid within the reservoir. For example, processor 26, or another component of IMD 12 or another device, e.g. programmer 20, may trigger an alarm related to the estimated volume of fluid in reservoir 34 of IMD 12, including e.g. audible, tactile, and/or visual alerts. In one example, a reservoir empty or full state alarm may include audible alerts issued by programmer 20 or another external device associated with therapy system 10. In another example, a reservoir fill status alarm includes IMD 12 vibrating within the body of patient 16, thereby providing a tactile alert. In other examples, the alarm includes text or graphical messages delivered to patient 16 and/or a clinician via text message or e-mail from programmer 20 or another electronic device communicatively connected to IMD 12 and/or programmer 20, thereby providing a visual alert. In one example, processor 26 may also trigger an alarm related to the rate at which a user, e.g. a clinician is adding fluid to or removing fluid from reservoir 34. For example, processor 26 may trigger an alarm in the event the rate at which a clinician adds fluid to reservoir 34 is estimated based on the measured pressure differential between a pressure measured by reservoir pressure sensor 42 and a pressure measured by propellant chamber pressure sensor 43 to be greater than or equal to a maximum recommended refill rate.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. A method comprising:
    measuring a pressure within a therapeutic fluid reservoir of an implantable fluid delivery device with a first pressure sensor;
    measuring a pressure within a chamber of the fluid delivery device at least partially surrounding the reservoir with a second pressure sensor;
    estimating a volume of a therapeutic fluid within the reservoir based on a pressure differential between the measured pressure within the reservoir and the measured pressure within the chamber, wherein estimating the volume comprises estimating a rate at which the therapeutic fluid is added to or removed from the reservoir based on the measured pressure within the reservoir and the measured pressure within the chamber; and
    displaying an indication of the estimated rate at which the therapeutic fluid is added to or removed from the reservoir.

2. The method of claim 1, wherein the chamber comprises a propellant gas chamber configured to store a propellant gas configured to regulate the pressure within the reservoir.

3. The method of claim 1, wherein estimating the rate at which the therapeutic fluid is added to or removed from the reservoir comprises estimating the rate based on a rate of change of the pressure differential over time and a pressure sensitivity to volume changes constant for the reservoir.

4. The method of claim 1, wherein estimating the volume of the therapeutic fluid within the reservoir comprises estimating the volume based on the estimated rate at which the therapeutic fluid is added to or removed from the reservoir and a baseline volume of therapeutic fluid in the reservoir.

5. The method of claim 4, wherein the baseline volume comprises a starting volume of therapeutic fluid in the reservoir when the therapeutic fluid is first added to or removed from the reservoir.

6. The method of claim 5, wherein estimating the volume of the therapeutic fluid within the reservoir comprises:
    multiplying the estimated rate at which the therapeutic fluid is added to or removed from the reservoir by a time over which the therapeutic fluid is added to or removed from the reservoir; and
    adding the starting volume to the estimated rate multiplied by the time.

7. The method of claim 1, further comprising displaying an indication of the estimated volume of the therapeutic fluid within the reservoir.

8. The method of claim 7, wherein displaying the indication of the estimated volume comprises displaying a volume gauge on a computing device communicatively connected to the fluid delivery device.

9. The method of claim 1, further comprising generating an alert when the estimated rate at which the therapeutic fluid is added to or removed from the reservoir is greater than or equal to a maximum recommended refill rate.

10. The method of claim 9, wherein the alert comprises at least one of an audible, visual, or tactile alert.

11. The method of claim 9, wherein generating the alert when the estimated rate at which the therapeutic fluid is added to or removed from the reservoir is greater than or equal to the maximum recommended refill rate comprises displaying an indication to slow down an actual rate at which the therapeutic fluid is added to or removed from the reservoir.

12. The method of claim 1, further comprising:
displaying an indication of one or more of a maximum recommended refill rate and a difference between the estimated rate at which the therapeutic fluid is added to or removed from the reservoir and the maximum recommended refill rate.

13. A fluid delivery system comprising:
an implantable fluid delivery device comprising:
  a reservoir configured to store a therapeutic fluid;
  a chamber at least partially surrounding the reservoir;
  a first pressure sensor configured to sense a pressure within the reservoir;
  a second pressure sensor configured to sense a pressure within the chamber;
  a display device; and
a processor configured to receive the sensed measurements of the pressure within the reservoir from the first pressure sensor, receive the sensed measurements of the pressure within the chamber from the second pressure sensor, and estimate a volume of a therapeutic fluid within the reservoir based on a pressure differential between the measured pressure within the reservoir and the measured pressure within the chamber,
wherein to estimate the volume, the processor is configured to estimate a rate at which the therapeutic fluid is added to or removed from the reservoir based on the measured pressure within the reservoir and the measured pressure within the chamber, and
wherein the processor is further configured to control the display device to display an indication of the estimated rate at which the therapeutic fluid is added to or removed from the reservoir.

14. The system of claim 13, wherein the chamber comprises a propellant gas chamber configured to store a propellant gas configured to regulate the pressure within the reservoir.

15. The system of claim 13, wherein to estimate the rate at which the therapeutic fluid is added to or removed from the reservoir, the processor is configured to estimate the rate based on a rate of change of the pressure differential over time and a pressure sensitivity to volume changes constant for the reservoir.

16. The system of claim 13, wherein to estimate the volume of the therapeutic fluid within the reservoir, the processor is configured to estimate the volume based on the estimated rate at which the therapeutic fluid is added to or removed from the reservoir and a baseline volume of therapeutic fluid in the reservoir.

17. The system of claim 16, wherein the baseline volume comprises a starting volume of therapeutic fluid in the reservoir when the therapeutic fluid is first added to or removed from the reservoir.

18. The system of claim 17, wherein to estimate the volume of the therapeutic fluid within the reservoir, the processor is configured to:
  multiply the estimated rate at which the therapeutic fluid is added to or removed from the reservoir by a time over which the therapeutic fluid is added to or removed from the reservoir; and
  add the starting volume to the estimated rate multiplied by the time.

19. The system of claim 1, wherein the processor is further configured to control the display device to display an indication of the estimated volume of the therapeutic fluid within the reservoir.

20. The system of claim 19, wherein to control the display device to display the indication of the estimated volume, the processor is configured to control the display device to display a volume gauge on a computing device communicatively connected to the fluid delivery device.

21. The system of claim 13, wherein the processor is further configured to generate an alert when the estimated rate at which the therapeutic fluid is added to or removed from the reservoir is greater than or equal to a maximum recommended refill rate.

22. The system of claim 21, wherein the alert comprises at least one of an audible, visual, or tactile alert.

23. The system of claim 21, wherein to generate the alert when the estimated rate at which the therapeutic fluid is added to or removed from the reservoir is greater than or equal to the maximum recommended refill rate, the processor is configured to control the display device to display an indication to slow down an actual rate at which the therapeutic fluid is added to or removed from the reservoir.

24. The system of claim 13, wherein the processor is further configured to:
  control the display device to display an indication of one or more of a maximum recommended refill rate and a difference between the estimated rate at which the therapeutic fluid is added to or removed from the reservoir and the maximum recommended refill rate.

25. A computer-readable storage medium comprising instructions for causing a programmable processor to:
  measure a pressure within a therapeutic fluid reservoir of an implantable fluid delivery device with a first pressure sensor;
  measure a pressure within a chamber of the fluid delivery device at least partially surrounding the reservoir with a second pressure sensor;
  estimate a volume of a therapeutic fluid within the reservoir based on a pressure differential between the measured pressure within the reservoir and the measured pressure within the chamber, wherein the instructions that cause the processor to estimate the volume comprise instructions that cause the processor to estimate a rate at which the therapeutic fluid is added to or removed from the reservoir based on the measured pressure within the reservoir and the measured pressure within the chamber; and
display an indication of the estimated rate at which the therapeutic fluid is added to or removed from the reservoir.

26. A system comprising:
  a first means for measuring a pressure within a therapeutic fluid reservoir of an implantable fluid delivery device;
  a second means for measuring a pressure within a chamber of the fluid delivery device at least partially surrounding the reservoir; and
  means for estimating a volume of a therapeutic fluid within the reservoir based on a pressure differential between the measured pressure within the reservoir and the measured pressure within the chamber, wherein the means for estimating the volume comprises means for estimating a rate at which the therapeutic fluid is added to or removed from the reservoir based on the measured pressure within the reservoir and the measured pressure within the chamber; and
  means for displaying an indication of the estimated rate at which the therapeutic fluid is added to or removed from the reservoir.

* * * * *